(12) United States Patent  
Bills

(10) Patent No.: US 6,972,008 B2
(45) Date of Patent: Dec. 6, 2005

(54) SYRINGE HAVING A TAPERED PLUNGER

(75) Inventor: Dan J. Bills, Salt Lake City, UT (US)

(73) Assignee: Ultradent Products, Inc., South Jordan, UT (US)

( * ) Notice: Subject to any disclaimer, the term of this patent is extended or adjusted under 35 U.S.C. 154(b) by 366 days.

(21) Appl. No.: 10/278,225

(22) Filed: Oct. 21, 2002

(65) Prior Publication Data

US 2004/0078006 A1 Apr. 22, 2004

(51) Int. Cl.[7] ............................................. A61M 5/315
(52) U.S. Cl. ..................................... 604/218; 604/187
(58) Field of Search ............................... 604/110, 218, 604/192, 263, 187, 239, 264, 265, 275, 279, 193, 181

(56) References Cited

U.S. PATENT DOCUMENTS

| | | | |
|---|---|---|---|
| 1,831,668 A | 11/1931 | Juhl | |
| 2,261,213 A | 11/1941 | Bierman | 128/214 |
| 3,277,922 A | 10/1966 | Eisel | 137/613 |
| 4,043,336 A | 8/1977 | Kreb, III | 128/218 R |
| 4,175,559 A | 11/1979 | Kreb, III | 128/218 R |
| 4,679,705 A | 7/1987 | Hamilton | 222/90 |
| 4,846,801 A | * 7/1989 | Okuda et al. | 604/218 |
| 4,931,044 A | 6/1990 | Beiter | 604/248 |
| 5,135,511 A | * 8/1992 | Houghton et al. | 604/220 |
| 5,178,186 A | 1/1993 | Levasseur | 137/556 |
| 5,814,017 A | * 9/1998 | Kashmer | 604/110 |
| 5,951,160 A | * 9/1999 | Ronk | 366/130 |
| 5,989,219 A | * 11/1999 | Villas et al. | 604/110 |

OTHER PUBLICATIONS

U.S. Appl. No. 10/106,397, filed Mar. 26, 2002, Bills.

* cited by examiner

*Primary Examiner*—Manuel Mendez
(74) *Attorney, Agent, or Firm*—Workman Nydegger

(57) ABSTRACT

Syringes of the invention include a barrel having a tapered outlet portion and a plunger that is conformingly tapered to enter the tapered portion of the barrel and to expel the fluid material contained within the tapered portion of the barrel. To help expel the material from the barrel, the syringes of the invention include sealing means that are configured to seal the stem of the plunger to the barrel. The sealing means may include one or more rings that circumferentially protrude away from the stem and slidably engage the inner surface of the barrel. In certain embodiments, the syringes also include applicator valves that are disposed at the outlet end of the barrel and that can be rotated between open and closed positions to control the flow of the fluid material out of the barrel.

19 Claims, 10 Drawing Sheets

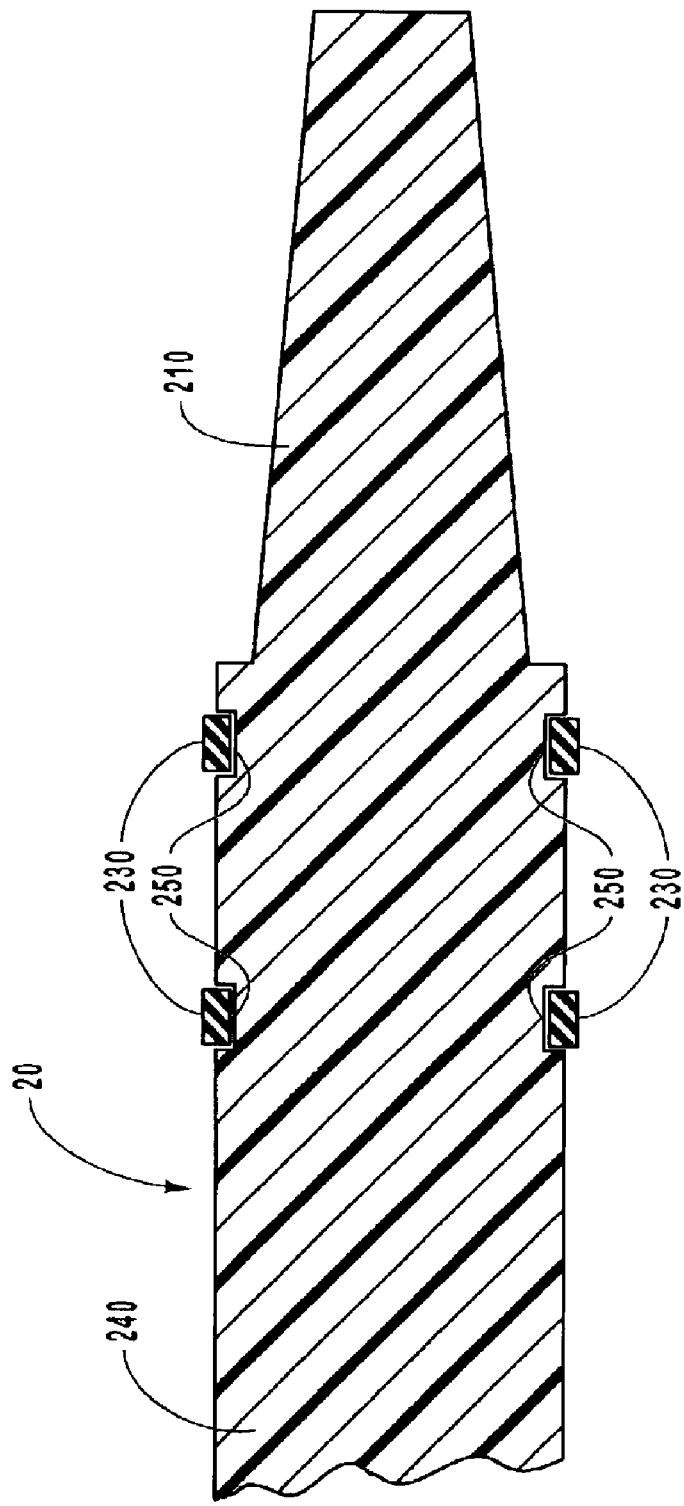

SYRINGE HAVING A TAPERED PLUNGER

BACKGROUND OF THE INVENTION

1. The Field of the Invention

The present invention is in the field of dental composition delivery systems and, more particularly, in the field of dental syringes.

2. The Relevant Technology

In the field of dentistry, dental compositions are often delivered through a syringe. While some syringes contain only enough composition for a single application, other syringes contain enough composition to be used a plurality of times on a single patient or on a plurality of patients.

One benefit of multi-dose syringes, over the single dose syringes, is that they are generally more cost efficient. One drawback of multi-dose syringes, however, is the difficulty of ensuring the syringe is properly sealed between uses to prevent undesired leakage and evaporation or premature curing of the composition within the syringe. For instance, the tips of existing syringes are typically sealed closed with threaded or friction fitting caps. However, there is a risk the closure caps will not be sufficiently tightened onto the tips of the syringes between uses because the existing syringes do not include means for indicating when the caps are sufficiently sealed or tightened onto the tips of the syringes. Yet another problem with multi-dose syringes is that the syringe caps or lids can easily be misplaced or lost, thereby preventing the syringes from being adequately sealed. When the cap is not sufficiently sealed on the tip of a syringe then the composition within the syringe can leak, evaporate, or prematurely cure, thereby minimizing the cost advantage of purchasing the larger capacity multi-dose syringes.

Another problem with certain syringes is that they have plungers that are not suitably configured to expel all of the material from the barrels. Accordingly, in view of the foregoing, there is currently a need in the art for improved syringe delivery systems.

SUMMARY OF PRESENTLY PREFERRED EMBODIMENTS

Briefly summarized, presently preferred embodiments of the present invention are directed to improved syringe delivery systems.

According to one presently preferred embodiment, the valve syringe of the invention includes a barrel configured for containing a fluid material, a plunger configured for pushing the fluid material to an outlet end of the barrel, and an applicator valve disposed at the outlet end of the barrel that is also configured to rotate between an open position and a closed position for controlling the flow of the fluid material through the applicator valve.

The applicator valve includes an internal contact surface configured to frictionally engage the tapered outlet end of the barrel for preventing the fluid material from flowing through the opening formed in the outlet end of the barrel when the applicator valve is in the closed position during periods of nonuse. The applicator valve also includes at least one relief slot formed in the internal contact surface that is configured to allow the fluid material to flow through the barrel opening when the applicator valve is in the open position during use. When the applicator valve is in the open position, the fluid material is able to flow through the applicator valve and into an applicator tip through which the fluid material is dispensed.

The tapered outlet end of the barrel also includes an inner surface that defines a tapered void. To accommodate this tapered inner portion of the barrel, the plunger of the invention is configured with a tapered end that is sized and shaped to conformingly engage the inner surface of the tapered portion of the barrel. This configuration enables the plunger to successfully expel substantially all of the fluid material that may reside within the tapered portion of the barrel.

The plunger also includes sealing means for sealing the stem of the plunger to the inner surface of the barrel. The sealing means effectively prevents leaking and undesired loss of the fluid material between the plunger and the barrel. According to one embodiment, the sealing means includes one or more flexible sealing rings that circumferentially protrude away from the stem proximate the tapered end of the plunger. The sealing rings are preferably configured to slidably engage the inner surface of the barrel and to prevent leaking of the fluid material between the stem and the barrel.

During use, the plunger is forced through the barrel, causing the fluid material to be expelled out of the opening formed in the tapered outlet portion of the barrel. The tapered portion of the plunger also helps to fully expel the fluid material out of the barrel when it is inserted into the tapered outlet portion of the barrel.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings in which:

FIG. 10 illustrates a cross-sectional side view of a portion of the plunger which illustrates a tapered portion of the plunger and sealing rings disposed about the stem of the plunger.

DETAILED DESCRIPTION OF THE PREFERRED EMBODIMENTS

A detailed description of the valve syringe of the invention will now be provided with specific reference to figures illustrating preferred embodiments of the invention. It will be appreciated that like structures will be provided with like reference designations.

In order to provide context for interpreting the scope of the invention, certain terms will now be defined. The term "composition," as used herein, refers to any fluid material or fluid composition of materials capable of being dispensed through a syringe. By way of example and not limitation, the compositions referred to herein include organic and synthetic compositions as well as water-based and solvent-based compositions. Although the terms "composition" and "fluid material" are used interchangeably herein, it will be appreciated that the compositions and fluid materials are not limited to having any particular viscosity. Rather the viscosity of the fluid materials can vary to accommodate different needs and preferences, but should be at least low enough to flow through the applicator valve and applicator tip during normal use.

The term "applicator tip," as defined herein, refers to any tip, tube, needle, cannula, or other dispensing device configured to dispense a fluid material and is characterized by the attribute of including at least a hollow or concave portion through which the fluid material can flow.

The term "luer taper," as used herein, refers to a standard luer taper of about six percent (6%) as described in document "ISO 594-2: 1998 Conical fittings with 6% (Luer) taper for syringes, needles and certain other medical equipment—Part 2: Lock fittings." However, it will be appreciated that the luer taper may also comprise other angles that are either less than or greater than six percent as desired.

The term "mating engagement formations," as defined herein, refers to any combination of engaging formations, including, but not limited to, recesses, ridges, protrusions, holes, latches, clips, knobs, pins, slots, tabs, and apertures which are configured to interconnect, internest, mate, lock, or otherwise frictionally engage.

The valve syringes of the invention, as described herein, are generally configured to control the flow of fluid material through an application valve disposed at the outlet end of a syringe barrel. During use, fluid material flowing through the application valve is dispensed through an application tip, which is either integrally connected to or detachably connected with the applicator valve.

I. Single Use Applicator Valve

Figure 1:
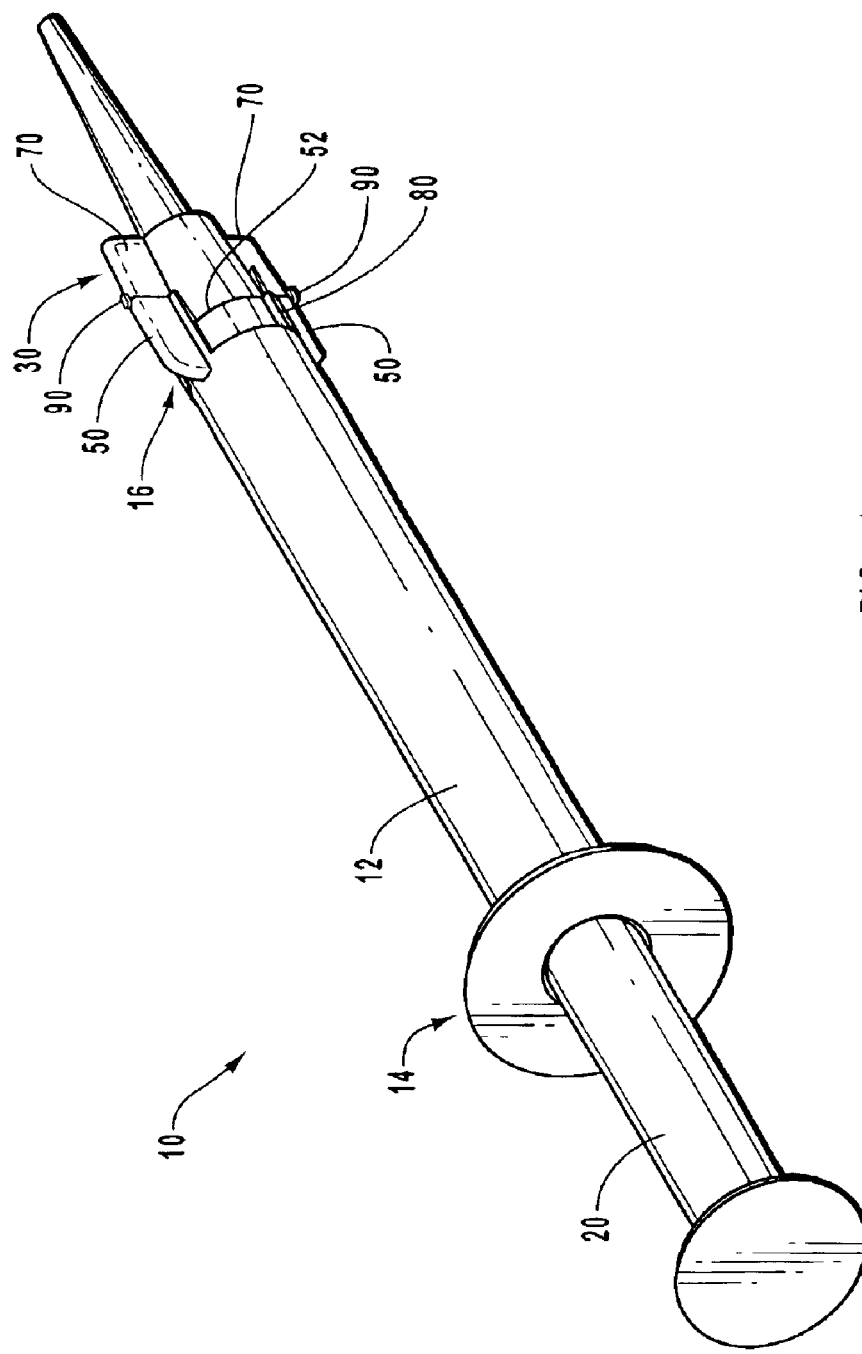
FIG. 1 illustrates a back perspective view of one embodiment of a valve syringe of the invention that includes a barrel configured for containing a fluid material, a plunger configured for pushing the fluid material to the outlet end of the barrel, and an applicator valve disposed at the outlet end of the barrel.

FIG. 1 illustrates one presently preferred embodiment of the valve syringe 10 of the invention. As shown, the valve syringe 10 generally includes a barrel 12 configured for containing a fluid material. The barrel 12 has a generally cylindrical cross-sectional shape and extends from an inlet end 14 to an outlet end 16. It will be appreciated that the cross-sectional shape of the barrel 12 may vary to accommodate various needs and preferences. The plunger 20, inserted within the inlet end 14 of the barrel 12, is specifically configured in shape and size for pushing the fluid material contained within the barrel 12 to the outlet end 16 of the barrel 12, where it is forced through and dispensed out of the applicator valve 30. The applicator valve 30 is preferably configured in size and shape for rotatably engaging the outlet end 16 of the barrel 12.

Figure 2:
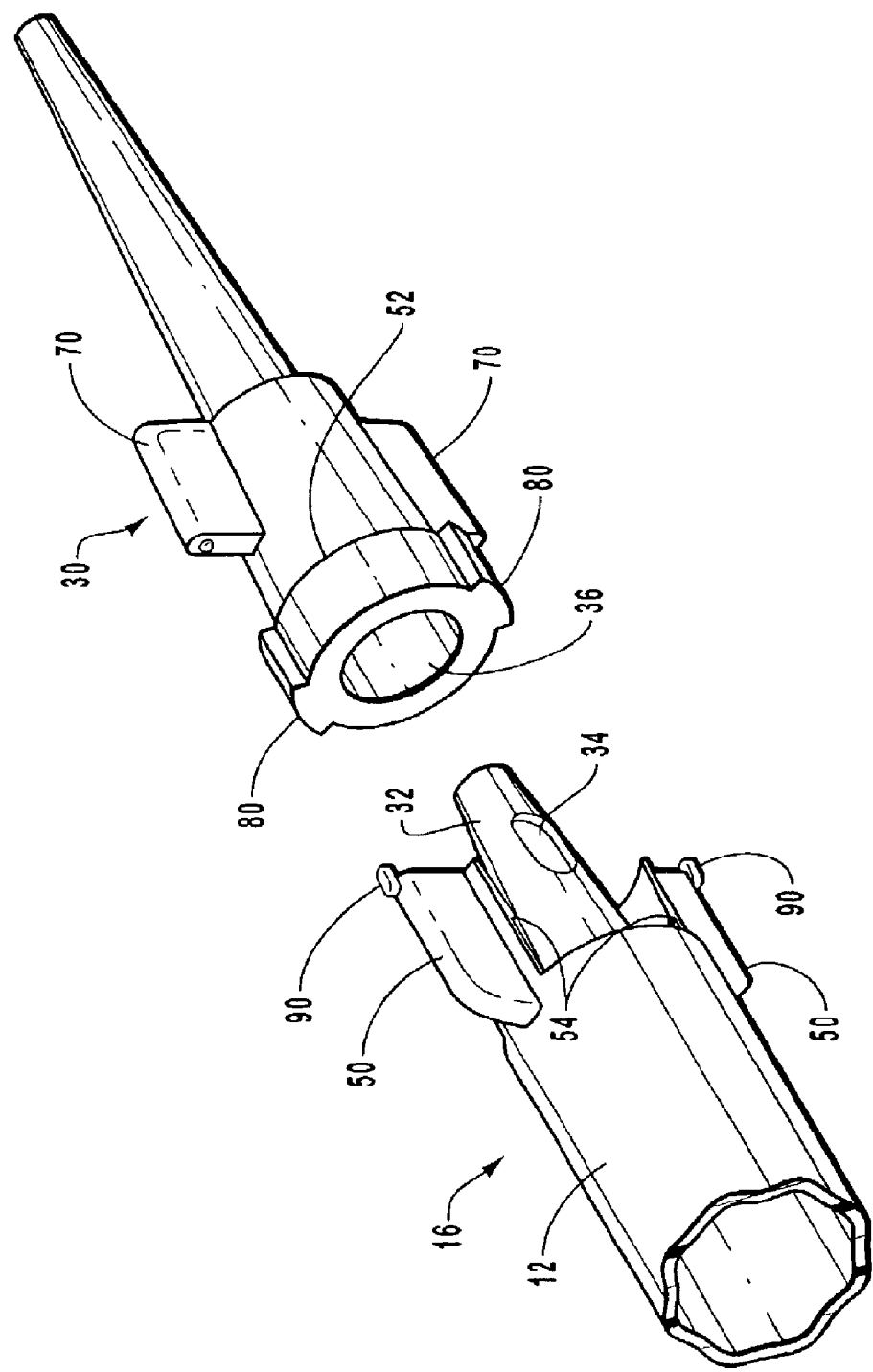
FIG. 2 illustrates an exploded perspective view of the outlet end of the barrel and the applicator valve.

FIG. 2 illustrates an exploded view of the applicator valve 30 and the outlet end 16 of the barrel 12. As shown, the outlet end 16 of the barrel 12 includes a sidewall 32 with at least one barrel opening 34 formed in the sidewall 32. The sidewall 32 is preferably tapered, such as with a standard 6% luer taper. It will be appreciated, however that the angle of the taper may vary to accommodate different needs and preferences.

According to one present embodiment, the valve syringe 10 includes two barrel openings 34 that are disposed in opposite sides of the sidewall 32, although only one of the barrel openings 34 can be seen in the illustration shown. In other embodiments, only a single opening 34 is present.

According to the preferred embodiment, the applicator valve 30 includes a contact surface 36 that is correspondingly tapered to abuttingly engage the outlet end 16 of the barrel 12. In particular, the contact surface 36 of the applicator valve 30 is configured in size and shape to engage the sidewall 32 of the outlet end 16 of the barrel 12 so as to prevent the fluid material from exiting through the barrel openings 34 when the applicator valve 30 is disposed in a closed position, as generally shown and described below in reference to FIG. 3.

Figure 3:
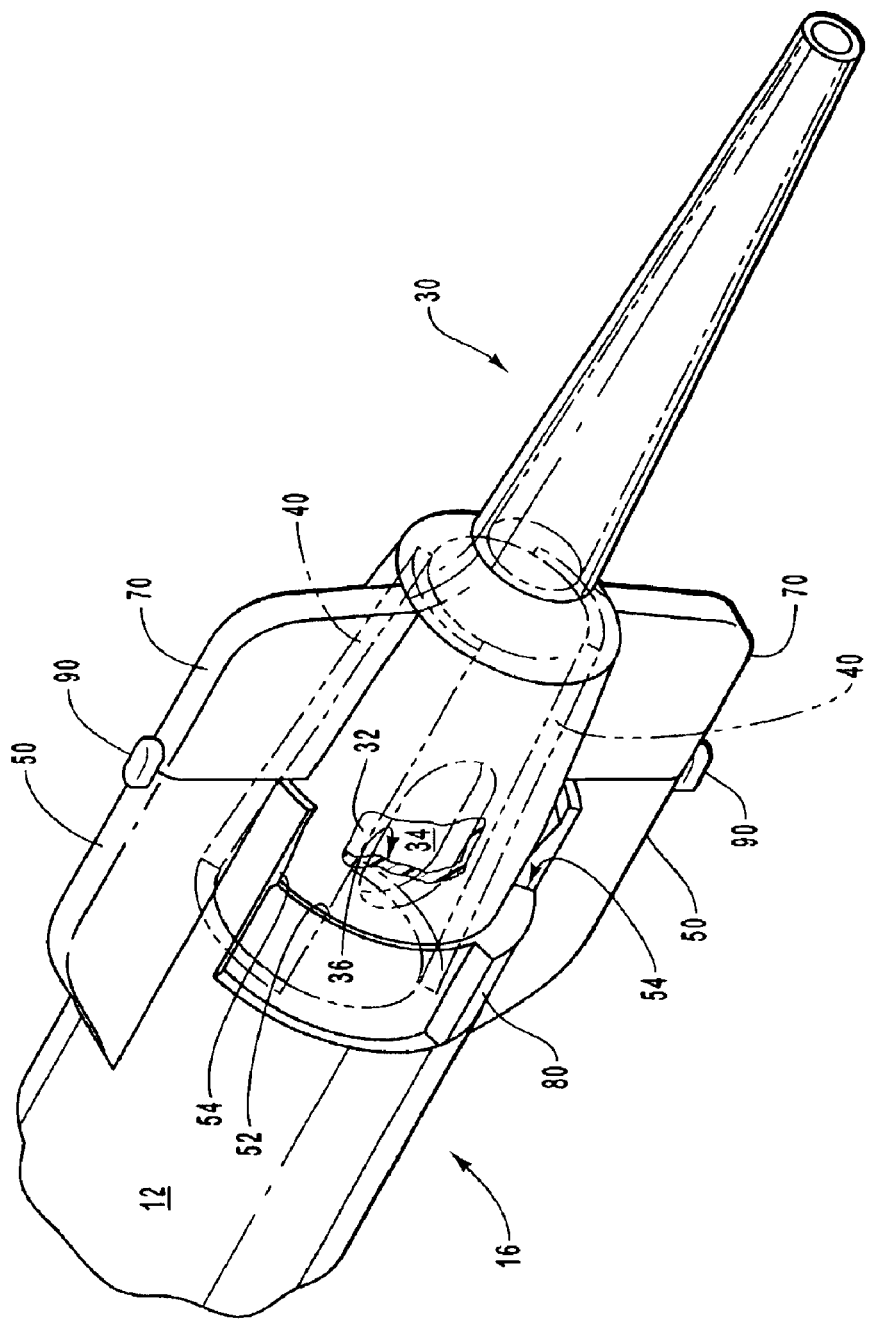
FIG. 3 illustrates a partial cross-sectional perspective view of the outlet end of the barrel and the applicator valve with the applicator valve disposed in the closed rotational position.

FIG. 3 illustrates a partial cross-sectional perspective view of the applicator valve 30 disposed on the outlet end 16 of the barrel 12 in a closed position. As shown, in the closed position, the contact surface 36 of the applicator valve 30 covers the barrel opening 34 to prevent the fluid material from passing therethrough.

Figure 4:
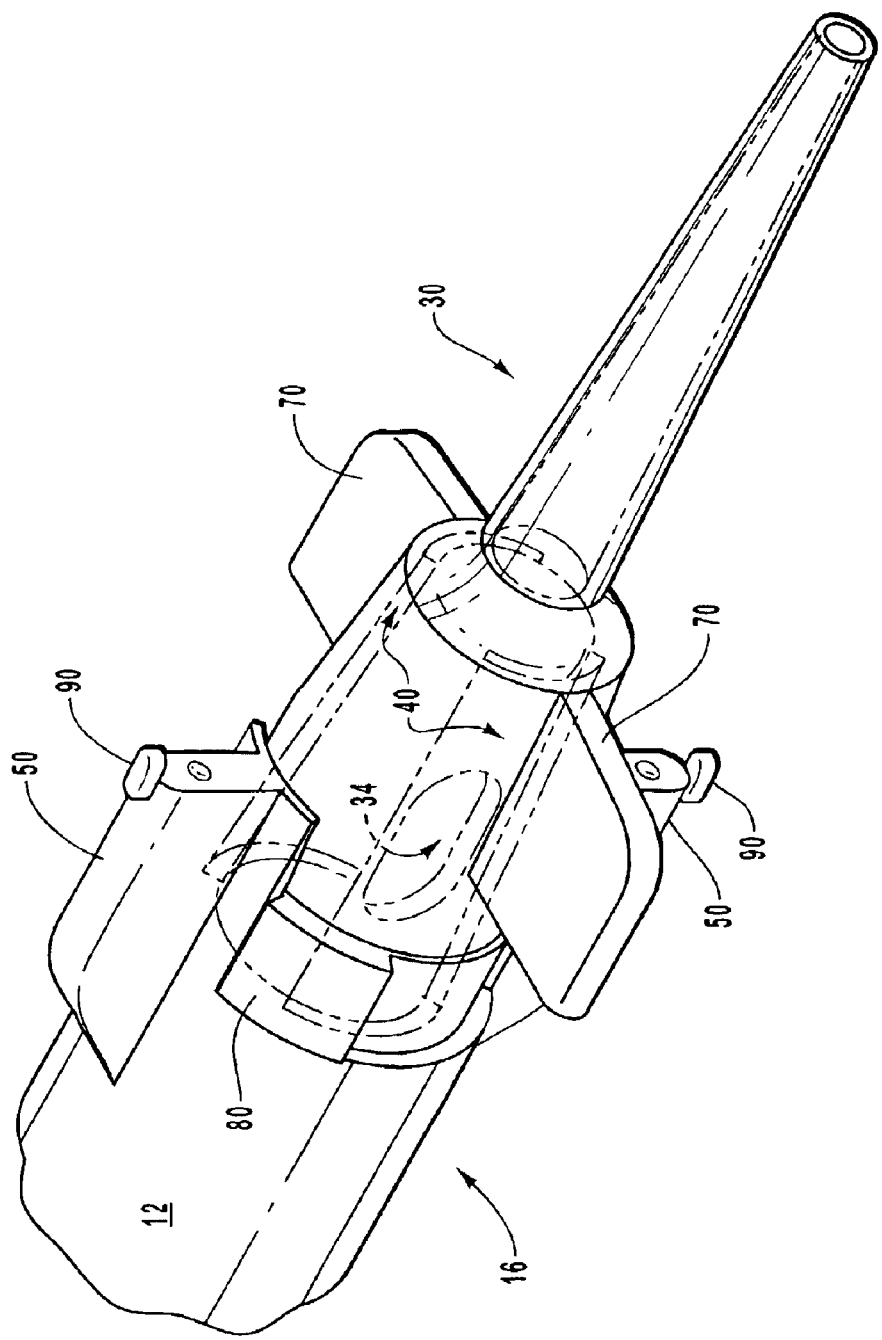
FIG. 4 illustrates a front perspective view of the outlet end of the barrel and the applicator valve with the applicator valve disposed in the open rotational position.

FIG. 4 illustrates the applicator valve 30 in an open position. As shown, relief slots 40 formed within the contact surface 36 of the applicator valve 30 at least partially align with the barrel openings 34 in the outlet end 16 of the barrel 12, although only one barrel opening 34 is presently visible in this view. This arrangement of the relief slots 40 and the barrel openings 34 is further clarified by the illustration shown in FIG. 5.

Figure 5:
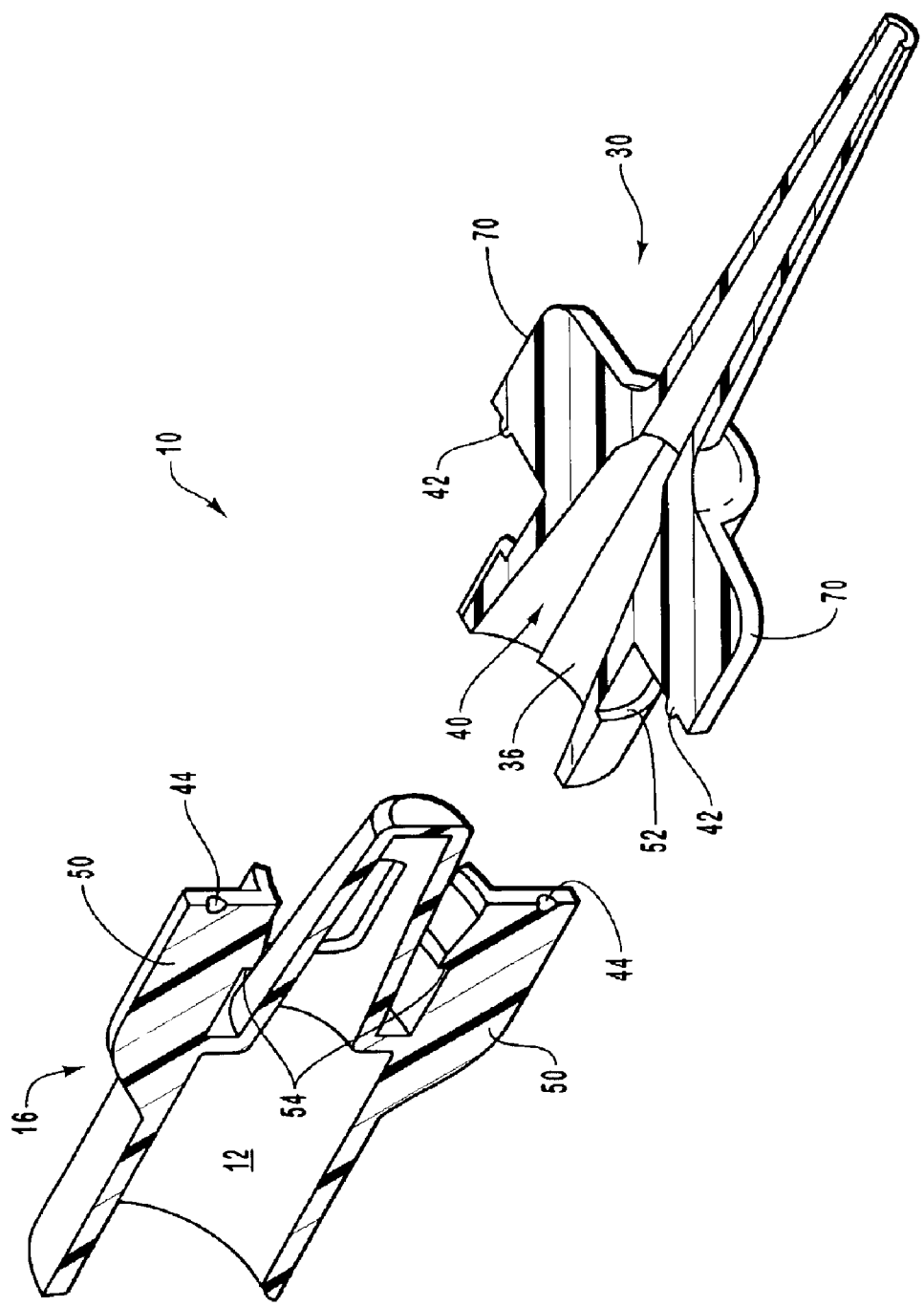
FIG. 5 illustrates a cross-sectional exploded view of the outlet end of the barrel and the application valve that also shows the alignment of the barrel opening and the relief slot when the application valve is rotationally aligned in the open position.

FIG. 5 illustrates an exploded cross-sectional view of the outlet end 16 of the barrel 12 and of the applicator valve 30. As shown, the applicator valve 30 is concentrically aligned with the barrel 12 and rotated with respect to the barrel in the rotational alignment of the open position shown in FIG. 4. It is evident that when the applicator valve 30 is disposed on barrel 12 in this rotational alignment, within an open position, that the barrel opening 34 at least partially aligns with the relief slot 40 formed into the contact surface 36 of the applicator valve 30. It should also be appreciated that by aligning the barrel opening 34 with the relief slots, in the open position, that the composition within the barrel will be able to flow through the barrel openings 34 and into the applicator valve through which it is dispensed during use. Flow can occur even when the openings are only partially aligned, although some restriction may occur depending on the degree of alignment.

FIG. 5 also illustrates securing means for releasably securing the applicator valve 30 in the closed position. In particular, knobs 42 and recesses 44 formed in the valve syringe 10 are configured to internest in mechanical engagement when the applicator valve 30 is disposed in the fully closed position, which is shown and described above in reference to FIG. 3. The securing means may also include any other combination of mating engagement formations, including, but not limited to, recesses, ridges, protrusions, holes, latches, clips, knobs, pins, slots, tabs, and apertures which are configured to interconnect, internest, mate, lock, or otherwise mechanically or frictionally engage when the applicator valve 30 is in the closed position.

It will be appreciated that the securing means of the invention are useful for at least enabling a user to know when the applicator valve 30 is completely rotated into the closed position. In this manner, the valve syringes 10 of the invention provide an improvement over prior art devices which include closure caps that do not have any means for indicating when the cap is sufficiently placed over the syringe to prevent the flow or evaporation of the fluid material contained therein. Instead, prior art devices require the user to repeatedly determine how tightly the closure cap must be placed on the syringe to prevent undesired leaking and evaporation of the fluid material contained within the syringe. In contrast, the securing means of the present invention enable a user to know exactly how far the applicator valve 30 must be rotated to secure the applicator valve 30 in the closed position. Once in the closed position, the securing means also prevent the applicator valve 30 from being inadvertently rotated into the open position. In this manner the securing means of the invention also provide an improvement over prior art devices that include closure caps that can easily become dislodged or unsecured during shipping, storage, and other periods of nonuse.

FIGS. 1–5 also illustrate retaining means for retaining the applicator valve 30 on the outlet end 16 of the barrel 12. In these presently shown embodiments, the retaining means includes tab members 50 extending from the outlet end 16 of the barrel 12 and a ridge member 52 circumferentially extending at least partially around the applicator valve 30. As shown, each of the tab members 50 includes a ledge 54 configured to slidably engage the ridge member 52 of the applicator valve 30 during rotation of the applicator valve 30 between the open and closed positions. In this manner the valve syringe 10 of the invention provides means for retaining the applicator valve 30 at the outlet end 16 of the barrel 12. It will be appreciated, however, that the applicator valve 30 can still be removed from the outlet end 16 of the barrel 12 by flexing the tab members 50 away from the barrel 12 until the ledges 54 clear the ridge member 52. This is useful, for instance, to enable the applicator valve 30 to be interchanged. It may be desirable to interchange the applicator valve 30 when the sanitation of the applicator valve 30 is compromised, such as may occur when the valve syringe 10 is dropped on the floor, or placed in a patient's mouth, for instance.

Although the barrel 12 of the valve syringe 10 can be configured for containing only enough composition for a single use, it can also be configured with a sufficiently large barrel 12 to contain multiple doses of the composition, in which case it is also desirable to interchange the applicator valve 30 between uses on different patients. It may also be desirable to interchange the applicator tip between uses on a single patient if a two-part composition has mixed and cured within the applicator tip. Yet another reason to interchange the applicator valve 30 is to utilize the special attributes of differently shaped and configured applicator tips. For instance, the applicator tip may be configured as a needle, as a cannula, as a flocked applicator, or any other configuration to accommodate different needs and preferences.

II. Multiple Use Applicator Valve

Figure 6:
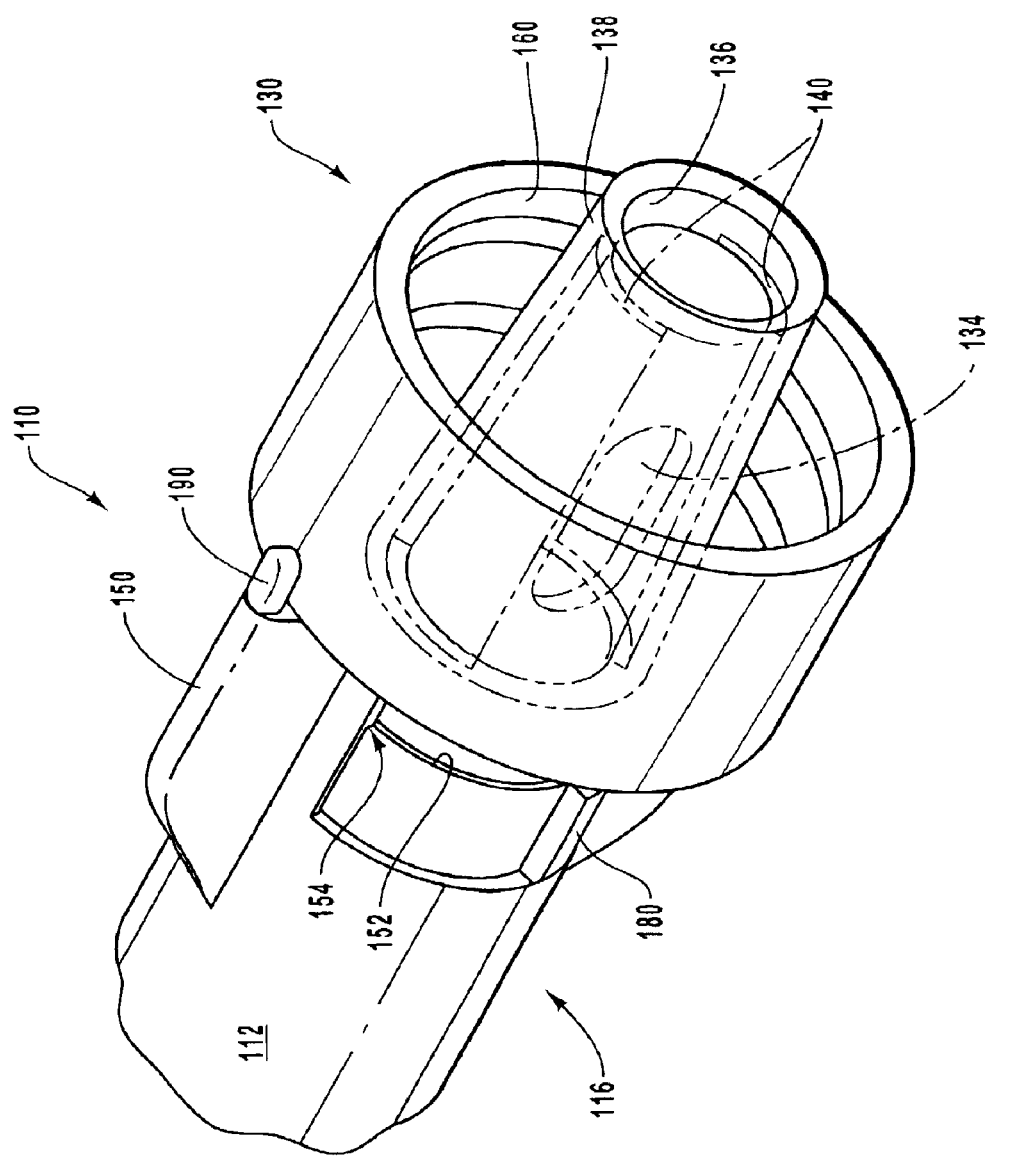
FIG. 6 illustrates one embodiment of the applicator valve that is disposed at the outlet end of the syringe barrel in a closed rotational position and which includes threaded coupling means for coupling the applicator valve to a threaded applicator tip.
Figure 7:
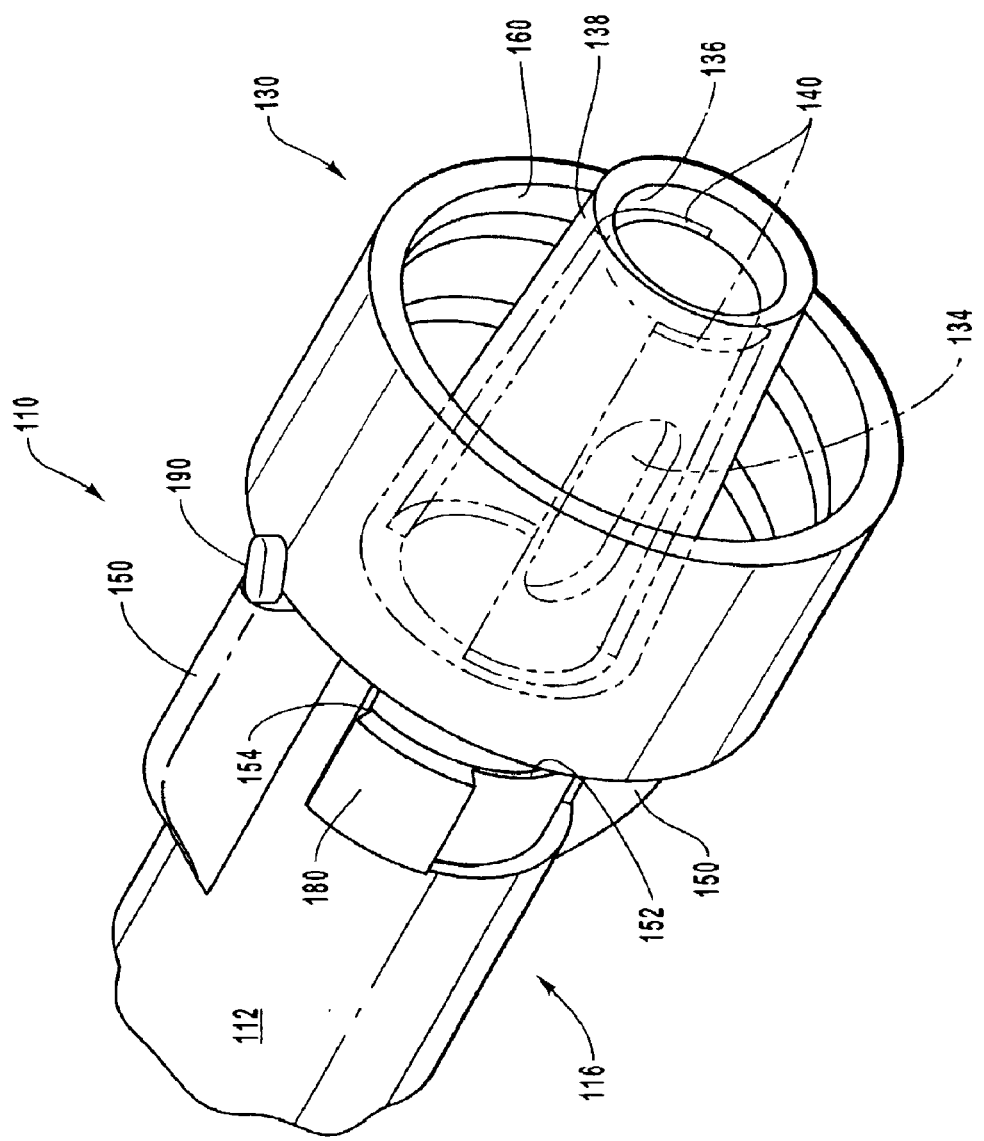
FIG. 7 illustrates one embodiment of the applicator valve that is disposed at the outlet end of the syringe barrel in an open rotational position and which includes threaded coupling means for coupling the applicator valve to a threaded applicator tip.

FIGS. 6–7 illustrate an alternative embodiment of the valve syringe 110 of the invention in which the applicator valve 130 is configured with coupling means for coupling the applicator valve 130 to interchangeable applicator tips without removing the applicator valve 130 from the barrel 112 of the valve syringe 110. This embodiment is particularly useful for preventing premature curing in applicator tips between uses.

As shown in FIG. 6, similar to the previous embodiments, the applicator valve 130 includes a contact surface 136 that is configured to block the flow of the fluid material when the applicator valve 130 is in the closed position. As shown in FIG. 7, the applicator valve 130 also includes relief slots 140 that are configured to align with the barrel openings 134 (only one is shown) and to allow the fluid material to flow through the applicator valve 130 when the applicator valve 130 is rotated into the open position, as in the previous embodiments. The valve syringe 110 of the present embodiment also includes retaining means for retaining the applicator valve 130 on the outlet end 116 of the barrel 112. In particular, the valve syringe includes a ridge 152 and corresponding ledges 154 which, as generally described above, slidably engage in a suitable manner for retaining the applicator valve 130 on the outlet end 116 of the barrel 112.

One difference between the present embodiment and the previously disclosed embodiments, however, is that the applicator valve 130 advantageously includes a threaded surface 160 that circumferentially extends around the applicator valve 130 which is configured for threadably engaging and coupling with threaded applicator tips. This threaded surface 160 comprises one suitable coupling means for coupling the applicator valve 130 to interchangeable applicator tips. To accommodate industry standards, the internal mating surface 138 of the applicator valve 130 may be configured with a luer taper.

The syringe of the present embodiment is preferably configured to contain multiple doses of composition to be used over a period of time on a plurality of applications. This embodiment is useful, for instance, to maximize the cost efficiency of selling, shipping and storing the composition in bulk quantities. Inasmuch as the valve syringe 110 is intended for repeated use, it is useful to provide the valve syringe 110 with the coupling means that have been described for facilitating the ability to interchange the applicator tips between uses and to preserve a desired level of sanitation between uses.

According to other embodiments, as illustrated in FIGS. 1–5, the valve syringes 10 of the invention also include rotation facilitating means for facilitating rotation of applicator valve 30 between the closed and open positions. For instance, according to this embodiment, the valve syringes 10 comprise wing members 70 that extending from the applicator valve 30 and configured to be engaged by the fingers of a user. The wing members 70 enable a user to apply more leverage during rotation of the applicator valve 30. In another embodiment, not shown, the rotation facilitating means includes a frictional surface on the applicator valve 110. To prevent over-rotation of the applicator valve 30 and 130, the valve syringes 10 and 110 may also include stopping means for stopping rotation of the applicator valve 30 and 130 once the applicator valve 30 and 130 is sufficiently rotated into the open and closed positions. As shown in FIGS. 1–4 and 6–9, the stopping means may include one or more radial block members 80 and 180 protruding away from the applicator valves 30 and 130 which are configured to engage the tab members 50 and 150 once the applicator valves 30 and 130 are completely rotated into the open and closed positions.

In yet another embodiment, the valve syringes 10 and 110 of the invention include tamper evident means for indicating whether the applicator valve 30 and 130 has rotated from the closed position to the open position at least one time. For instance, as shown in FIGS. 1 and 3, bridge members 90 fixedly interconnecting the applicator valve 30 and the barrel 12 at the tab members 50 enables a user to visually determine whether the applicator valve 30 has been rotated out of the closed position. The bridge members 90 are noticeably and irreversibly broken, as shown in FIG. 4, when the applicator valve 30 is rotated from the closed position to the open position for the first time.

FIGS. 6–7 illustrate one alternative embodiment of how the tamper evident means can be used with the valve syringes of the invention. As shown, the tamper evident means includes a bridge member 190 that interconnect the applicator valve 130 and the barrel 112 at the general location of the tab member 150. According to this embodiment, the bridge member 190 is noticeably and irreversibly broken when the applicator valve 130 is rotated from the closed position to the open position for the first time. Despite the specific examples provided above, however, it should be appreciated that the tamper evident means can include any number of bridge members that interconnect any portions of the barrel 112 and the applicator valve 130 and are not, therefore, necessarily disposed at the general location of the tab members 50 and 150.

III. Tapered Plunger

Figure 8:
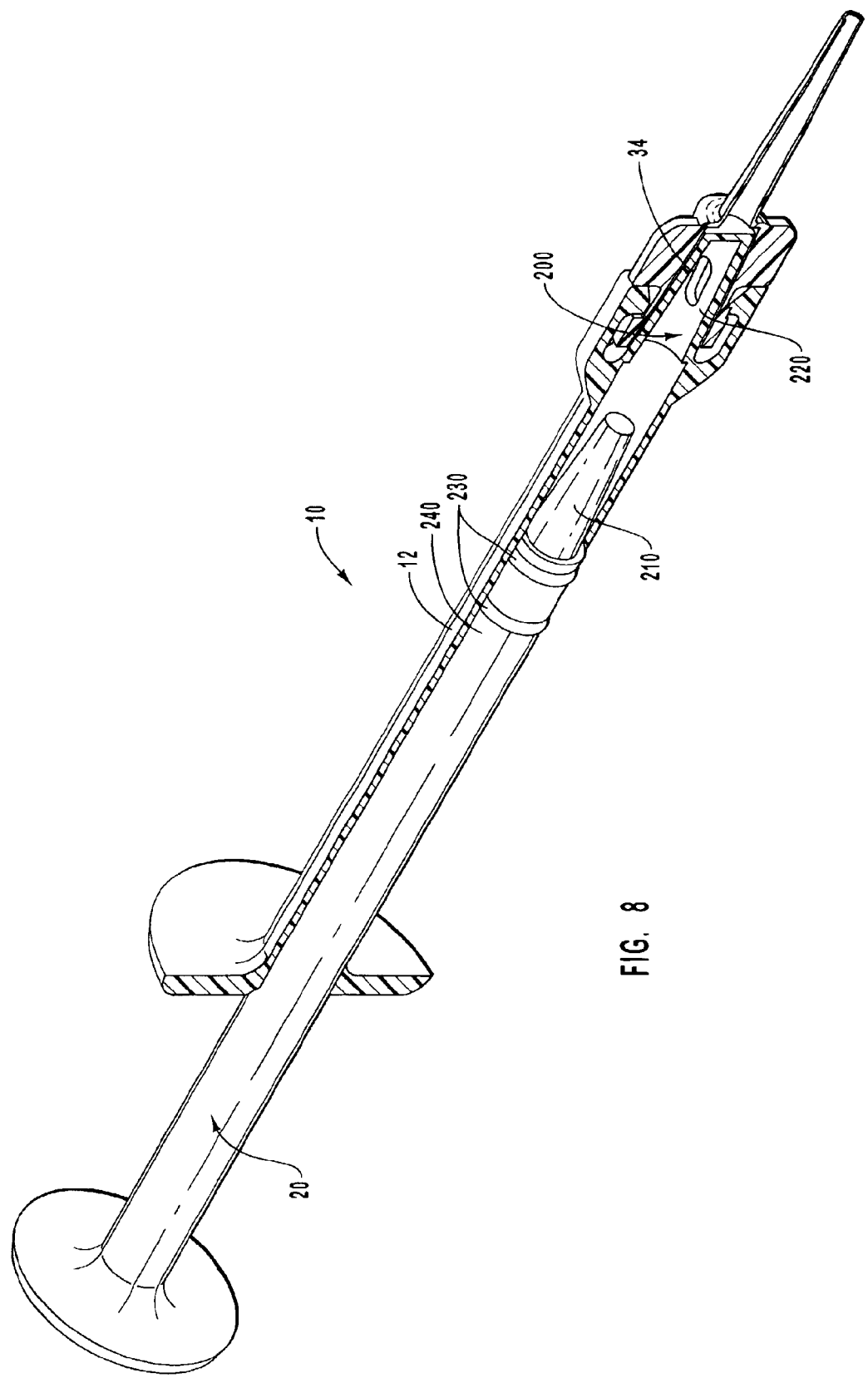
FIG. 8 illustrates a perspective cutaway view of a syringe in which the barrel includes a tapered portion and in which the syringe includes a plunger having a tapered tip.

Attention is now directed to FIG. 8, which illustrates a partial cross-sectional view of the syringe of FIG. 1. As shown, the plunger 20 of the syringe 10 is specifically configured to expel fluid material out of the opening 34 that is formed in the tapered portion 200 of the barrel 12. In particular, the plunger 20 includes a first end 210 that is tapered and configured in size and shape to conformingly engage the inner surface 220 of the tapered portion 200 of barrel 12. The taper of the plunger 20 and the barrel 12 may include a luer taper or any other taper.

The plunger of the invention also includes sealing means for sealing the plunger 20 within the barrel 12. In particular, the plunger 20 includes one or more sealing rings 230 that protrude away from the stem 240 of the plunger 20 and that are located proximate the tapered end 210 of the plunger 20. Accordingly, although the present embodiment illustrates a plunger 20 having two rings 230, it will be appreciated that the plunger 20 can also be configured with a single ring 230 or with more than two rings 230. One benefit of using two or more sealing rings 230 is that the plunger 20 may be more capable of pushing the fluid material through the barrel without allowing any material to leak past the sealing rings 230. A plurality of rings 230 may also provide a greater seal between the stem 240 and the barrel 12, so as to prevent premature leaking and evaporation of the fluid material when the syringe 10 is stored and transported.

The rings 230 are preferably configured to slidably engage the inner surface of the barrel 12 and to create a seal between the stem 240 of the plunger 20 and the barrel 12. This enables the plunger to push the fluid material towards and through the opening formed in the tapered portion 200 of the barrel 12.

Figure 9:
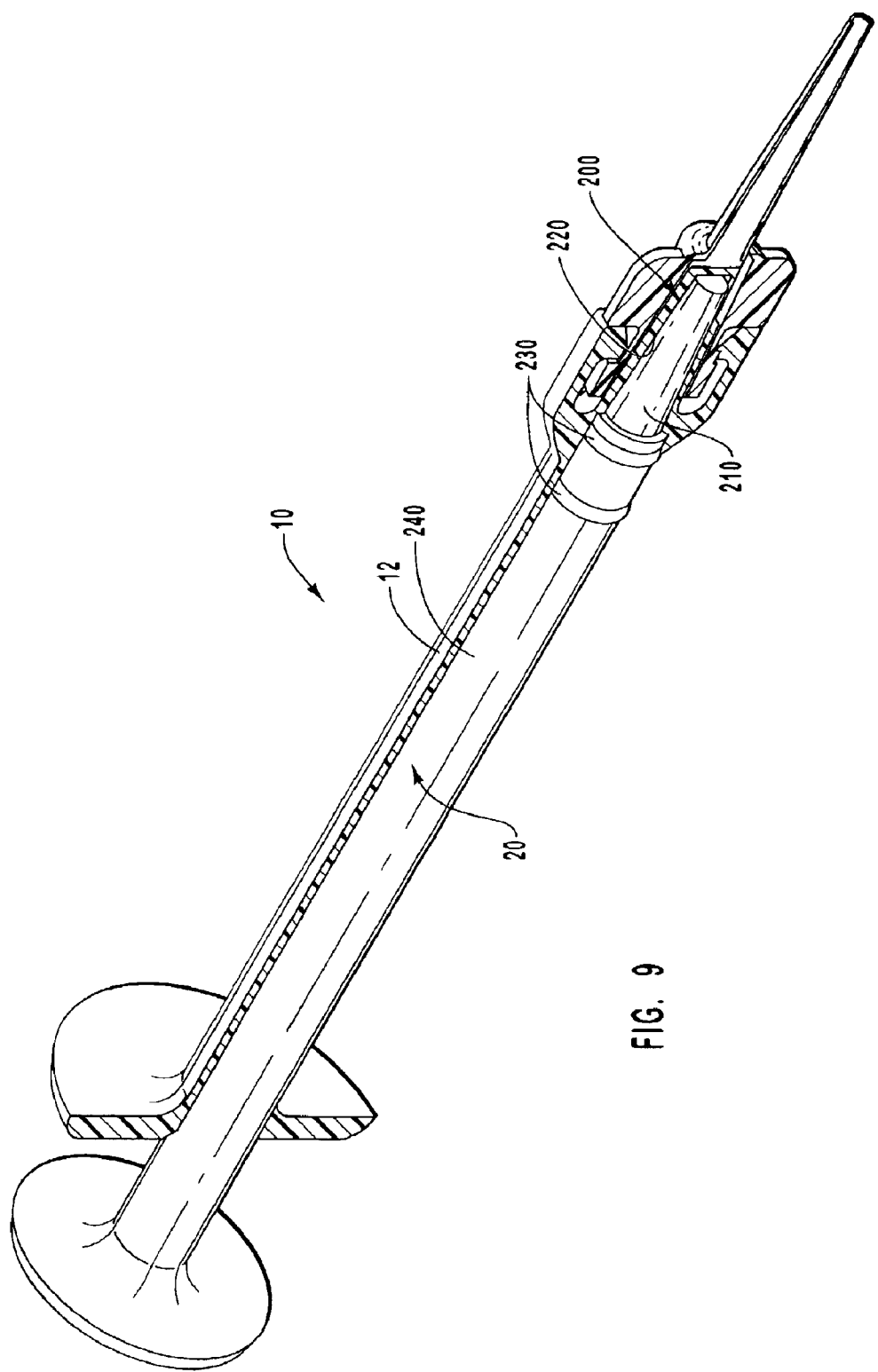
FIG. 9 illustrates a perspective cutaway view of the syringe shown in FIG. 8 in which the plunger is fully inserted within the barrel of the syringe, such that the tapered portion of the plunger is inserted within the tapered portion of the barrel.

FIG. 9 illustrates how the tapered end of the plunger 20 is specifically configured to engage the inner surface 220 of the tapered end 200 of the barrel 12. It will be appreciated that this configuration is useful for enabling the plunger 20 to successfully expel substantially all of the fluid material that may be contained within the tapered end 200 of the barrel 12 out of any openings that are formed in the tapered end 200 of the barrel 12, such as the opening 34 that is illustrated in FIG. 8. It will also be appreciated that this configuration is useful for minimizing any wasted product or residual fluid material that would otherwise remain within the barrel 12.

FIG. 10 illustrates a cross-sectional side view of a portion of the plunger 20 that shows the tapered end 210 and sealing rings 230 of the plunger 20. As shown, the sealing rings 230 may be detachably attached to the stem 240 of the plunger 20. For instance, in the present embodiment, the rings are detachably secured to the stem 240 of the plunger 20 within recesses 250 that are formed in the stem 240. It will be appreciated, however, that the rings 230 may also be integrally formed or attached to the stem 240 such as with a two-color injection molding process in which the rings 230 are fixedly molded to the stem 240.

Although the rings 230 are shown to have a substantially rectilinear cross-sectional area, it will also be appreciated that the rings 230 can be formed with round, angled or irregular cross-sectional areas. The material of the sealing rings 230 may comprise the same material that is used to form the stem 240 or a different material. According to one embodiment, the sealing rings 230 are composed of a flexible or a semi-rigid plastic or elastomeric material. It will be appreciated, however, that the material composition of the rings 230 may comprise any material that is suitable for creating a seal between the stem 240 and the barrel 12. Non-limiting examples of materials that may be used to manufacture the sealing rings 230 include polyethylene, polypropylene, nylon, Teflon, polycarbonate, natural or synthetic rubber, silicone, other elastomers, and thermoset plastics.

During use, the plunger is forced through the barrel, towards the outlet end of the barrel, causing the fluid material to be expelled out of the opening formed in the outlet end of the barrel. While the plunger is forced through the barrel, the sealing rings slidably engage the inner surface of the barrel, forcing the fluid material forward, preventing leaking of the fluid material between the stem and the barrel. Then, once the tapered end of the plunger is finally inserted into the tapered outlet portion of the barrel, the tapered end of the plunger is able to completely expel any residual amounts of the fluid material that may remain within the tapered portion of the barrel.

It will be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. A syringe for containing and dispensing a fluid material, the syringe comprising:
   a barrel configured for containing a fluid material, the barrel including an inlet end and an outlet end, wherein the outlet end includes a tapered portion having an inner surface that defines a tapered void, and wherein at least one barrel opening is formed in a sidewall of the tapered portion of the barrel through which the fluid material can flow;
   a plunger including:
      a stem extending from a first end that is disposed within the barrel to a second end that is disposed outside of the barrel, wherein the first end of the stem is configured in size and shape to enter the tapered portion of the barrel and to substantially conformingly engage the inner surface of the tapered portion of the barrel; and
      sealing means for creating a seal that extends circumferentially about the plunger between the stem and the barrel, wherein the sealing means is disposed on the stem proximate the first end of the stem; and
      a valve that is disposed in rotational alignment with the barrel and in abutting engagement with the tapered portion of the barrel, such that the valve controls passage of the fluid material from the at least one barrel opening when the valve is rotated with respect to the barrel.

2. A syringe as recited in claim 1, wherein the sealing means includes at least one ring that circumferentially extends around the stem in such a manner as to engage an inner surface of the barrel, such that the ring slidably engages the inner surface of the barrel when the plunger is moved within the barrel.

3. A syringe as recited in claim 2, wherein the ring is composed of a flexible material.

4. A syringe as recited in claim 2, wherein the ring is composed of at least one of plastic and rubber.

5. A syringe as recited in claim 6, wherein the ring and the plunger are composed of the same material.

6. A syringe as recited in claim 2, wherein the ring is integrally attached to the stem.

7. A syringe as recited in claim 3, wherein the ring is integrally attached to the stem in a two-color molding process.

8. A syringe as recited in claim 1, wherein the first end of the stem is configured in size and shape to expel fluid material contained within the tapered portion of the barrel out of the at least one barrel opening when the first end of the stem is inserted within the tapered portion of the barrel.

9. A syringe as recited in claim 1, further including an applicator valve disposed at the outlet end of the barrel and configured to rotate between an open position and a closed position, including:
   an internal contact surface configured to engage the outlet end of the barrel in a manner so as to prevent the fluid material from exiting through the barrel opening when the applicator valve is in the closed position, and
   at least one relief slot formed in the internal contact surface and configured to allow the fluid material to pass through the at least one barrel opening and into the at least one relief slot when the applicator valve is in the open position.

10. A syringe as recited in claim 9, wherein the internal contact surface of the valve is correspondingly tapered to abuttingly engage the tapered portion of the barrel so as to prevent the fluid material from exiting through the at least one barrel opening when the valve is set in a closed position.

11. A syringe as recited in claim 9, wherein the at least one barrel opening comprises at least two barrel openings.

12. A syringe as recited in claim 1, wherein the first end of the stem is configured in size and shape to expel fluid material contained within the tapered portion of the barrel out of the barrel opening when the first end of the stem is inserted within the tapered portion of the barrel.

13. A syringe as recited in claim 1, wherein the tapered portion comprises a luer taper.

14. A syringe for containing and dispensing a fluid material, the syringe comprising:
   a barrel configured for containing a fluid material, the barrel including an inlet end and an outlet end, wherein the outlet end includes a tapered portion having an inner surface that defines a tapered void, and wherein a barrel opening is formed in the tapered portion of the barrel through which the fluid material can flow;
   a plunger including:
      a stem extending from a first end that is disposed within the barrel to a second end that is disposed outside of the barrel, wherein the first end of the stem is configured in size and shape to enter the tapered portion of the barrel and to conformingly engage the inner surface of the tapered portion of the barrel; and
      at least one ring disposed proximate the fist end of the stem that protrudes away from the stem and that circumferentially extends around the stem, the ring being configured to create a seal between the stem and an inner surface of the barrel; and
      a valve that is disposed in rotational alignment with the barrel and in abutting engagement with the tapered portion of the barrel, such that the valve controls passage of the fluid material from the at least one barrel opening when the valve is rotated with respect to the barrel.

15. A syringe as recited in claim 14, wherein the ring is detachably attached to the stem.

16. A syringe as recited in claim 14, wherein the ring is configured to slidably engage the inner surface of the barrel when the plunger is moved within the barrel.

17. A syringe as recited in claim 14, wherein the ring is composed of a semi-rigid material.

18. A syringe as recited in claim 14, wherein the ring is composed of at least one of plastic and rubber.

19. A syringe as recited in claim 18, wherein the ring and the plunger are composed of the same material.

* * * * *

UNITED STATES PATENT AND TRADEMARK OFFICE
CERTIFICATE OF CORRECTION

PATENT NO. : 6,972,008 B2 Page 1 of 1
APPLICATION NO. : 10/278225
DATED : December 6, 2005
INVENTOR(S) : Dan J. Bills It is certified that error appears in the above-identified patent and that said Letters Patent is hereby corrected as shown below:

Column 9
Line 43, change "claim 6" to --claim 4--

Column 10
Line 38, change "fist" to --first--

Signed and Sealed this

Fourth Day of March, 2008

JON W. DUDAS
*Director of the United States Patent and Trademark Office*